United States Patent [19]

Liehr

[11] Patent Number: 4,605,649

[45] Date of Patent: Aug. 12, 1986

[54] METHOD OF TREATMENT OF ESTROGEN DEFICIENCY DISEASE

[76] Inventor: Joachim G. Liehr, 115 Beverly La., Bellaire, Tex. 77401

[21] Appl. No.: 594,067

[22] Filed: Mar. 28, 1984

Related U.S. Application Data

[63] Continuation-in-part of Ser. No. 468,519, Feb. 22, 1983, abandoned.

[51] Int. Cl.⁴ .............................................. A61K 31/56
[52] U.S. Cl. .................................................... 514/182
[58] Field of Search ................. 424/238, 243; 514/182

[56] References Cited

U.S. PATENT DOCUMENTS

| 4,340,602 | 7/1982 | Brooks | 424/243 |
| 4,496,555 | 1/1985 | Brooks | 424/243 |

OTHER PUBLICATIONS

Hertz, "Cancer", 38 (1976) p. 534.
Goodman and Gilman's, "The Pharmacological Basis of Therapeutics (Chapter 6), pp. 1426–1431.

*Primary Examiner*—Albert L. Roberts
*Attorney, Agent, or Firm*—Charles W. Ashbrook; James L. Rowe

[57] ABSTRACT

2,4-Difluoro-$\beta$-estradiol, 2-fluoro-$\beta$-estradiol, and related fluoro estrogens used to treat estrogen-deficiency states in human females with genetic predisposition to cancer of estrogen-sensitive tissues.

12 Claims, No Drawings

METHOD OF TREATMENT OF ESTROGEN DEFICIENCY DISEASE

CROSS-REFERENCE

This application is a continuation-in-part of my application Ser. No. 468,519, filed Feb. 22, 1983, now abandoned.

BACKGROUND OF THE INVENTION

Prolonged treatment of experimental animals with exogenous estrogens including the steroid hormones—estrone, estradiol and estriol—has been reported to induce tumors of the testes, endometrium ovary, cervix and lymphoid tissues, mammary tissue, adrenal cortex, kidney, and anterior pituitary gland. Synthetic estrogens such as DES have also been found to increase the number of tumors in the same tissues in experimental animals.

The exact mechanism of tumor induction by these hormones is unknown. It has even been stated that the role of estrogens on the etiology of breast cancer and other gynecologic cancers may be permissive rather than causative. However, the ultimate question is, "Does the administration of estrogens under certain conditions, in certain dosages and for a certain length of time increase the incidence of neoplasms in responsive tissues?" [Hertz, Cancer, 38, 534 (1976)]. Various epidemiological studies indicate, without proving, that use of estrogen by post-menopausal women is associated with an increased risk of endometrial cancer [Goodman & Gilman-The Pharmacological Basis of Therapeutics, 6th Ed.—pp. 1426, 1429-30 (McMillan, New York 1980)].

It has been proposed, however, that the ring A polyhydroxylated estrogens, the primary products of estradiol or estrone metabolism, although almost devoid of estrogenic activity themselves, could be responsible for the carcinogenic or carcinopromoting action of estradiol. These polyhydroxy metabolites, 2- and 4-hydroxyestradiol or 2- and 4-hydroxyestrone, (catechols or ortho-dihydroxybenzenes) are the major biotransformatory products of estradiol in most species and are known to bind covalently in vitro to protein or peptides and to DNA. Such binding to protein can be suppressed by prior methylation of the catechol.

If oxidation of the phenolic ring of an estrogen is indeed a necessary step in the chain of events leading to increased numbers of tumors in experimental animals, then interference with metabolic oxidations might inhibit cancer induction by estrogens. Following this hypothesis, Li and Li, Proc. 72nd Annual Meeting Am. Assoc. Can. Res., 22, 11 (1981), were able to inhibit diethylstilbestrolinduced renal carcinoma in Syrian hamsters by chronic administration of inhibitors of microsomal cytochrome P-450 enzymes (oxidation enzymes). Another potential approach to prevention of carcinogenesis induction by estrogens would be to modify the estrogen structure so as to prevent oxidation to a catechol. Krey et al., Catechol Estrogens, Ed-Merriam & Lipsett, pages 249-263, (Raven Press, N.Y. 1983), investigating sexual behavior, such as loridosis, in female rats, found that there is reduced catechol estrogen formation with 2-fluoroestradiol and 4-fluoroestradiol—see FIG. 1, page 260. The authors conclude that catechol estrogen formation is not necessary for lordosis. Catechol estrogens had been shown to be precursors for reactive intermediates possibly responsible for tissue injury—Nelson et al., Biochem. Biophys. Res. Comm., 70, 1157 (1976).

The tumorigenicity of dibenzo(a,i)pyrene has been reduced by fluorination at 2,3 and/or 10. It is postulated that oxidation of the hydrocarbon ring to a catechol may be involved in tumor production by this compound.

There is apparently a genetic predisposition to cancer of estrogen dependent tissues in human females. The risk of breast cancer, where there is a family history of such tumor in first degree relatives, is increased 2-3 times [CMA Journal, 121, 505-8 (1979)]. With such persons, the increased risk of cancer potentially induced by administration of estrogen for treatment of estrogen-deficiency states weighs heavily against such estrogen replacement therapy. Stated in somewhat simpler terms, a human female with a history of greater than normal cancers of the breast, cervix, uterus or ovaries in her female relatives will, in many instances, have to endure the menopause rather than to be able to alleviate hot flashes and other menopausal symptoms by taking an estrogen, all for fear of incurring cancer. It is to such a group of human females, those with a genetic predisposition to cancer of estrogen sensitive tissues, that this invention is particularly directed.

It is thus an object of this invention to provide an estrogen of decreased cancer induction potential for use in treating menopause or other estrogen deficiency state in human females.

DESCRIPTION OF THE INVENTION

In fulfillment of the above and other objects, this invention provides a method for alleviating the effects of estrogen-deficiency disease in human females having a genetic predisposition to cancer of estrogen-sensitive tissues comprising the administration of a dose of a steroid according to structure I sufficient to alleviate the symptoms of said estrogen-deficiency disease without increasing the risk in said human female of the development of cancer of estrogen-sensitive tissues.

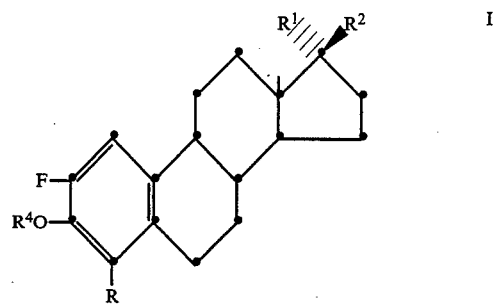

wherein R is H or F; when taken singly $R^1$ is H or ethinyl, and $R^2$ is OH; and when taken together, $R^1$ and $R^2$ are O=; and $R^4$ is H or $CH_3$, but can be $CH_3$ only when $R^1$ is not H.

Compounds falling within the scope of the above formula include:
2-fluoro-3,17β-estradiol
2,4-difluoro-3,17β-estradiol
2-fluoroestrone
2,4-difluoroestrone
2-fluoro-17α-ethinyl-3,17β-estradiol
2,4-difluoro-17α-ethinyl-3,17β-estradiol
2-fluoro-17α-ethinylestradiol 3-methyl ether 2,4-difluoro-17α-ethinylestradiol 3-methyl ether While only the 3-methyl ethers of the 17α-ethinyl compounds have been illustrated above as useful derivatives of the basic fluoroestrogens listed above, it will be appparent to those skilled in the art that other derivatives such as the 3-benzoate, 3,17-dipropionate, 3-cypionate (cyclopentylpropionate), 3,17-undecylate, 17-valerate and the like could be employed in my novel processes.

Human females falling within the above category in whom risk of cancer of estrogen-sensitive tissues is high are those in whose first degree relatives—parents, siblings, children—there have developed one or more cancers of estrogen-sensitive tissues.

The most prevalent estrogen-deficiency condition is menopause which can occur naturally after age 40 or can be induced by destruction of ovarian function, either surgically or by irradiation. Since most human females who survive to age 50 will have entered menopause and since menopausal symptoms are not only unpleasant but may include eventually osteoporosis, it is common to treat menopause by making up the estrogen deficiency of menopause by administration of estrogen. Commonly prescribed estrogens for alleviation of menopausal symptoms include DES (diethylstilbestrol), conjugated equine estrogens, (equilin, estrone etc.), β-estradiol, ethinyl estradiol, mestranol, hexestrol and dienestrol. Obviously, an estrogen with lowered potential for inducing cancer of estrogen sensitive tissues would be invaluable, particularly for those human females with a genetic predisposition to such tumors.

Another use of steroid estrogens such as mestranol and ethinyl estradiol has been as a component of oral contraceptives. Although the estrogen dosages for use in the oral contraceptive are less than those used for treatment of menopausal symptoms, product literature for these estrogen warns against the use of estrogen-containing oral contraceptives in women with known tumors of the breast, uterus, etc. However, there is insufficient information of a probative nature to determine at this time whether oral contraceptive users have an increased incidence of cancer of estrogen-dependent tissues. Obviously, it may be advantageous to use 2-fluoro-β-estradiol, 2-fluoro-17α-ethinylestradiol or other fluoro estrogens coming within the scope of the above formula, as the estrogenic component of an oral contraceptive, because of the lowered cancer incidence which may be associated with its use.

There is, however, a second property of 2-fluoro-β-estradiol and other fluoro estrogens represented by I above which may make their use in the relief of estrogen deficiency states or in oral contraceptives advantageous. This second property is their resistance to metabolism. Thus, less 2-fluoro-β-estradiol, 2-fluoro-17α-ethinylestradiol or other fluoro estrogen coming within the scope of formula I may be required to achieve an equal estrogenic effect since circulating estrogen levels with the fluoro estrogen will remain adequate for a longer period of time per dose. The fact that less estrogen can be used is probably not as important in reducing cancer incidence as in reducing the incidence of other diseases such as embolism frequently associated with estrogen administration in an oral contraceptive. While the quantity of circulating estrogen may be the same because of the longer half-life of the fluoro estrogen of formula I, the absolute quantity of drug will clearly be less. This lessened incidence of side effects not related to neoplastic incidence or growth is an added advantage of my novel therapeutic processes.

In order to demonstrate the decreased incidence of estrogen-induced tumors with the fluoro estrogens of formula I, specifically 2-fluoro-β-estradiol, compared to estradiol itself, the following experiments were carried out. First, the estrogenicity of the two compounds plus that of the isomeric 4-fluoro-β-estradiol were measured by two different methods. In one method, increase in wet uterine weight in ovariectomized, immature rats upon administration of estrogen was determined. The results of this test showed that the fluorinated estrogens were approximately as estrogenic as estradiol. The following protocol was used:

Female Sprague/Dawley rats, 3-4 weeks of age, were ovariectomized. Four days after ovariectomy animals were separated into four groups of equal group weight (17 animals/group, average weight: 90±1 g/animal) and estrogen treatment was begun. The animals received s.c. injections of 3.5 mcg. of estrogen in 0.7 ml. of saline/animal once daily for three days. Saline solutions were prepared by dissolving the estrogen in ethanol and diluting this solution with saline until a 5% ethanol/95% saline mixture was obtained. The control group received only saline. On the fourth day, the animals were killed, the uteri were excised, freed of luminal fluid and weighed. Data presented in Table 1 below are averages of wet uterine weights in mg. and the corresponding standard deviations.

In a second method, the weights of both testes of those male Syrian hamsters which were used in the in vivo carcinogenicity assay, were measured on the 224th day after s.c. implantation of 25 mg. pellets of estrogen. The weights were measured in grams (expressed as percent of total body weight). Treatment of animals with modified estrogens or with estradiol resulted in the shrinking of the testes to approximately 10% of the weights of testes in untreated hamsters.

The following protocol was employed:

Male Syrian hamsters, 3-4 weeks of age (Harlan/Sprague Dawley, Madison, Wis.), were given a 25 mg. s.c. implant consisting of 10% cholesterol and 90% estrogen. A second 25 mg. pellet of the same composition was implanted 106 days after the initial estrogen treatment. Estrogen treatment was carried out according to the procedure of Kirkman—National Cancer Institute Monograph, 2, 1-57 (1959). Control animals were left untreated. Two hundred twenty-four days after treatment with estrogens had begun, hamsters were weighed, killed, both testes were excised and their weights measured in grams. Data presented in Table 1 are the ranges of testes weights from four animals in each group. Weights are expressed as percentages of total body weights.

The results of these two tests are set forth in Table 1. In the table, column 1 gives the name of the compound under test, column 2 the uterine wet weights found and column 3 the weights of testes of male hamsters (as percent of total body weight).

TABLE 1.

| | Estrogenic Activity of Estradiols | |
|---|---|---|
| Compound | Range Of Testes Weight Of Male Hamsters [% Of Total Body Weight] | Uterine Wet Weights Of Female Rats [mg] ± s.d. |
| 2-fluoro-β-estradiol | 0.18-0.25 | 92-20 |
| 4-fluoro-β-estradiol | 0.18-0.28 | 118-19 |

TABLE 1-continued

| | Estrogenic Activity of Estradiols | |
|---|---|---|
| Compound | Range Of Testes Weight Of Male Hamsters [% Of Total Body Weight] | Uterine Wet Weights Of Female Rats [mg] ± s.d. |
| estradiol | 0.12–0.26 | 114–20 |
| control | 1.85–2.06 | 33–6 |

The above estrogenicity measurements compare well with experiments reported by Heiman et al., *J. Med. Chem.*, 23, 994 (1980) who reported the estrogen receptor binding affinities of the fluorinated estrogens. When expressed as ratios of association constants ($K_a$compound/$K_a$estradiol)×100, the binding affinity of 2-fluoro-β-estradiol was found to be 86, that of 4-fluoro-β-estradiol was 128.

Pfeiffer et al., *Proc. Soc. Neuroscience*, 8, 52 (1982)—measured the estrogen receptor affinity of 2- and 4-fluoro-β-estradiol in cytosol of the hypothalamus-preoptic area, the pituitary, and the uterus. The fluorinated estradiols were found to have high receptor affinity. Furthermore, biological responses of the fluorinated estrogens, such as elicitation of luteinizing hormone surges, of proceptivity, and of lordosis behavior in rats were, according to Krey et al., (loc. cit.), comparable with those elicited by estradiol.

The carcinogenicity of the modified estrogens was measured in male Syrian hamsters in vivo. Estrogen, and estrogen alone, causes renal clear cell carcinoma in 100% of the male animal population when exposed to s.c. estrogen implants. This kidney tumor is estrogen-induced and estrogen-dependent for development and growth. Failure to resupply estrogen every three months or surgical removal of implants results in tumor regression within a few weeks. Similarly, a tumor cell line, derived from the Syrian hamster renal clear cell carcinoma was found to be strongly estrogen dependent in vivo showing a 90% tumor regression 10 days after removal of the source of estrogen. The spontaneous kidney tumor incidence in Syrian hamsters without estrogen treatment is very low. The above facts are fully discussed in Kirkman, *Nat'l. Can. Inst. Monograph*, 1, 1 (1959); McGregor et al., *J. Nat'l. Can. Inst.*, 24, 1057 (1960) and Sirbasku et al., *Endocrin.*, 98, 1260 (1976).

The protocol employed was that set out for determining estrogen activity in male hamsters according to Table 1 (in that the animals examined for tumors at 224 days were the source of the testes). In the carcinogenicity experiment, further groups of animals were examined at 279 and 345 days. The animals were decapitated, the kidneys were excised and inspected visually for the occurrence of renal celear-cell carcinoma. Sections were prepared of all kidneys and studied histologically. The results of the histologic examinations are set forth in Table 2 below. In the table, column 1 gives the name of the compound, column 2 the total number of animals, column 3, the number of dead or lost animals and columns 4, 5 and 6 results of histologic examination of animals at the specified time interval for renal clear-cell carcinoma.

TABLE 2

| | | | No. of Animals with Tumors/ No. of Animals Examined on Various Days after s.c. Implantation of Estrogen | | |
|---|---|---|---|---|---|
| Compound | No. of Animals | No. of Lost or Dead* | 224 Days | 279 Days | 345 Days |
| Estradiol | 18 | 5 | 4/4 | 5/5 | 0/4 |
| 2-fluoro-β-estradiol | 15 | 3 | 0/4 | 0/4 | 0/3 |
| 4-fluoro-β-estradiol | 15 | 2 | 1/4** | 3/6 | 0/3 |
| Control | 10 | 0 | 0/3 | 0/3 | 0/4 |

*Number of animals lost or dead from various causes during the course of the experiment. Tumors appear approximately six months after pelleting with estrogen. Therefore, this group included all hamsters found dead during the first six months of the experiment, since tumors were not expected and not evident in the kidneys of these animals. Hamsters found dead after six months were also included in this group, if their kidneys could not be recovered. One dead hamster with recoverable kidneys was included in the nearest examination group at 279 days (animal treated with 4-fluoro-β-estradiol without renal carcinoma).
**2 of 4 judged histologically to be preneoplastic.

In Table 2, the fact that animals sacrificed at 345 days after implantation were tumor free probably indicates a decrease in circulating estrogen and a regression of the tumors present at 224 days or at 279 days.

It is apparent from the data in Table 2 that 2-fluoro-β-estradiol has a greatly decreased potential for induced renal clear cell carcinomas compared with estradiol or 4-fluoro-β-estradiol at equal estrogen dosages. It is also apparent that merely blocking the ortho oxidation of estradiol to a catechol as in 4-fluoro-β-estradiol is insufficient by itself to eliminate estrogen-induced renal clear cell carcinomas in hamsters. 2-Fluoro-β-estradiol is thus highly estrogenic yet non-carcinogenic in the particular animal model. As far as I know, the above finding is the first to separate estrogenicity and carcinogenicity in the estrogenic hormones.

The fluoroestradiols used in the dose experiments were synthesized according to the procedure of Utne et al., *J. Org. Chem.*, 33, 2469 (1968).

An alternate method of preparing 2-fluoro-β-estradiol, in admixture with 2-fluoroestrone, is given in French Pat. No. 4878M, Mar. 18, 1965.

An improved method of preparing 2-fluoro-β-estradiol has been developed by Ward and Jones—see Ser. No. 564,595 filed Dec. 22, 1983. This procedure uses 3,17β-estradiol diacetate, a known compound, as a starting material. This compound is mercurated at C-2 as with mercuric trifluoroacetate. The trifluoroacetylmercury group is replaced by fluorine upon treatment with acetylfluoride, after which step the diacetate groups are hydrolyzed to yield 2-fluoro-β-estradiol. A more detailed description of the Ward-Jones process follows.

About 10 g. of 17β-estradiol-17β-diacetate were dissolved in 15 ml. of trifluoroacetic acid and the solution cooled to about 0° C. Twelve grams of mercuric trifluoroacetate were added and the reaction mixture stirred at ice bath temperatures for about 3.5 hours. The solvent was then removed by evaporation in vacuo and the residual material dissolved in methylene dichloride. The methylene dichloride solution was extracted with water and the water wash discarded. The methylene dichloride layer was dried with anhydrous sodium sulfate. The drying agent was removed by filtration and the methylene dichloride evaporated from the filtrate in vacuo. The residual foam was triturated with hexane by sonication for about one hour to produce crystals. The crystallization mixture was filtered and the filter cake rinsed with hexane. About 17.2 g. of the 2-trifluoroacetylmercury derivative were obtained (92% yield).

Acetyl hypofluorite reagent was prepared as follows. A suspension of 5 g. of sodium acetate in 50 ml. of glacial acetic acid was added to 550 ml. of Freon 11 with stirring. The mixture was cooled to about −80° C. in a dry ice-acetone bath while nitrogen was being bubbled through the reaction mixture. When the reaction mixture had attained the desired temperature, a stream of 18% fluorine in nitrogen was bubbled in. After five to six hours, a 2 ml. aliquot was added to 20 ml. of 60% aqueous acetic acid containing 1.5 g. of potassium iodide. The iodine generated was completely oxidized by 5.8 ml. of 0.1N sodium thiosulfate which indicated that the solution was approximately 0.145 molar in acetyl hypofluorite.

Two grams of 2-trifluoroacetylmercury-17$\beta$-estradiol diacetate were dissolved in 25 ml. of chloroform. To this stirred solution was added 25 ml. of the 0.145 molar acetyl hypofluorite mixture prepared as described above. After about 10 minutes, the mixture was combined with other similar reaction mixtures. The combined reaction mixtures were then washed with water, with aqueous saturated sodium bicarbonate and again with water. The extracts were then dried. Evaporation of the solvent in vacuo yielded a residual yellowish oil.

Thirty-eight similar runs employing a total of 76 g. of the 2-trifluoroacetylmercury-17$\beta$-estradiol diacetate starting material were combined and the combined residues obtained after workup were chromatographed over silica gel using a 10% ethyl acetate—90% isoctane solvent mixture as the eluant. Those fractions containing 2-fluoro-17$\beta$-estradiol diacetate as determined by NMR analysis were combined to give 9.5 g. of the desired compound. This material was dissolved in toluene and rechromatographed over a Prep 500 silica gel column with toluene as the eluant. Seven and seven tenths grams of the desired 2-fluoro-17$\beta$-estradiol diacetate were thus obtained.

Three and six tenths grams of 2-fluoro-17$\beta$-estradiol diacetate were suspended in 48 ml. of methanol and 15 ml. of water. A solution of 2.4 g. of potassium hydroxide in 29 ml. of water was added. The reaction mixture was stirred overnight at ambient temperature. The volatile constituents were removed in vacuo and the resulting residue suspended in 1N aqueous hydrochloric acid. This suspension was slurried with ethyl acetate until two clean layers formed. The aqueous layer was separated and the separated layer washed with additional ethyl acetate. The ethyl acetate extracts were combined and the combined extracts washed twice with water and then dried. The combined solutions were concentrated to less than 50 ml. and crystallization induced by scratching. The crystallizing solution was placed at about 0° C. overnight. Crystals thus produced were separated by filtration and the filter cake washed with pre-cooled methanol. Two and nine hundredths grams of 2-fluoro-17$\beta$-estradiol were obtained in this way. The compound crystallized with $\frac{1}{2}$ mole of methanol.

Analysis for the hemimethanolate of 2-fluoro-17$\beta$-estradiol was as follows:

Calculated: C, 72:51; H, 8.22:
Found: C, 72.30; H, 8.49.

2-Fluoro-3,17$\beta$-estradiol can be converted to 2-fluoro estrone and that compound in turn converted to 2-fluoro-17$\beta$-ethinyl-3,17$\beta$-estradiol by standard procedures useful in preparing 17$\alpha$-ethinyl-$\beta$-estradiol from 17$\beta$-estradiol and/or estrone—see also French Pat. No. 4878M referred to above. The corresponding 3-methyl ethers, 17-esters, etc. are also preparable by standard procedures used in preparation of the corresponding non-fluorinated derivative.

For use in treatment of estrogen deficiency states such as the menopause compounds coming within the scope of formula I, such as 2-fluoro-$\beta$-estradiol and 2-fluoro-17$\alpha$-ethinyl estradiol, can be formulated for oral administration in the form of tablets containing 1-2 mg. of drug per tablet. Preferably, the drug is micronized before incorporation into tablets and care is taken in tabletting not to fuse the microscopic particles into larger aggregates. Another useful solid formulation would be a buccal tablet incorporating 2-fluoro-$\beta$-estradiol as the estrogenic drug. A commonly used method of administering $\beta$-estradiol itself is by implanting a 25 mg. pellet subcutaneously. The pellet pays out less than 2 mg./day of the drug. 2-Fluoro-$\beta$-estradiol can be similarly pelleted and implanted. An intramuscular suspension of 2-fluoro-$\beta$-estradiol in sterile, isotonic saline is also a satisfactory formulation. If a depot effect is desired, a suspension in a vegetable oil such as sesame oil should be used. The daily dose of compounds coming within the scope of formula I such as 2-fluoro-17$\alpha$-ethinyl estradiol, 2,4-difluoro-$\beta$-estradiol, 2,4-difluoro-17$\alpha$-ethinyl estradiol and 2-fluoro-$\beta$-estradiol etc. is 1-2 mg. but should not exceed the upper limit. If pellets or depot formulations are employed, the estrogenic pay out (amount released to the female body) should be 2 mg. or less per day.

Esters of 2-fluoro-$\beta$-estradiol can also be employed in IM suspensions to give an added depot effect, such esters including for example the 3-benzoate, the 3,17-dipropionate and the 17-cyclopentylpropionate. With these IM formulations, the rate of release should not be greater than 2 mg./day of 2-fluoro-$\beta$-estradiol equivalent. Thus, where esters are used, the highest daily dose of ester should be no higher than a dose equivalent to 2 mg. of 2-fluoro-17-$\beta$-estradiol.

The 3-methyl ethers of 2-fluoro-17$\alpha$-ethinyl estradiol and 2,4-difluoro-17$\alpha$-ethinyl estradiol are particularly useful as the estrogenic component of a typical oral contraceptive regimen, and are used at dosage rates 100–200% of that of mestranol, the corresponding unfluorinated compound.

I claim:

1. The method of alleviating menopausal symptoms in human females having an inherited susceptibility to cancer of estrogen sensitive tissues which comprises administering to said menopausal female a menopausal symptom relieving dose of a compound of the formula

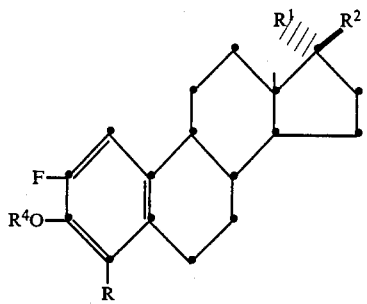

wherein R is H or F; $R^1$, when taken singly, is H or ethinyl; $R^2$, when taken singly, is OH; $R^1$ and $R^2$, when taken together, are O= and $R^4$ is H or $CH_3$, but can be $CH_3$ only when $R^1$ is not H, not to exceed 2 mg./day, thereby reducing the probability of said human female developing cancer in estrogen sensitive tissues induced by the ingestion of estrogens to relieve menopausal symptoms.

2. In the treatment of menopause or other estrogen deficiency disease in human females having a high genetic predisposition for cancer of estrogen sensitive tissues, the improvement which comprises the administration to such a female of an amount of a compound of the formula

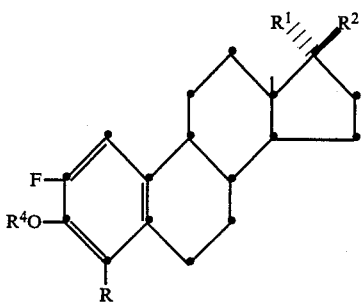

wherein R is H or F; $R^1$ when taken singly, is H or ethinyl; $R^2$, when taken singly is OH; $R^1$ and $R^2$ when taken together, are O= and $R^4$ is H or $CH_3$ but can be $CH_3$ only when $R^1$ is not H, sufficient to relieve symptoms of estrogen deficiency, but not to exceed 2 mg./day, while simultaneously reducing the chance of development of cancer of estrogen sensitive tissues ordinarily developing on estrogen treatment in such females.

3. A process for treating estrogen deficiency disease in human females without increasing the incidence of neoplasms of estrogen-sensitive tissues which comprises administering an estrogenic dose of a compound of the formula

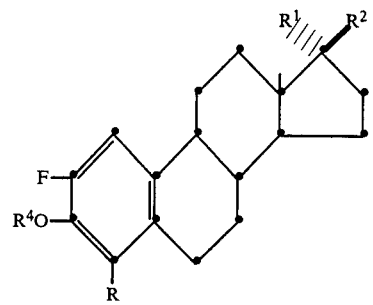

wherein R is H or F; $R^1$, when taken singly, is H or ethinyl; $R^2$, when taken singly is OH; $R^1$ and $R^2$ when taken together, are O= and $R^4$ is H or $CH_3$ but can be $CH_3$ only when $R^1$ is not H, sufficient to overcome said deficiency to such human female, but not to exceed 2 mg./day, on a daily basis.

4. A method for alleviating the effects of estrogen-deficiency disease in human females having a genetic predisposition to cancer of the estrogen sensitive tissues comprising the administration of a dose of a compound of the formula

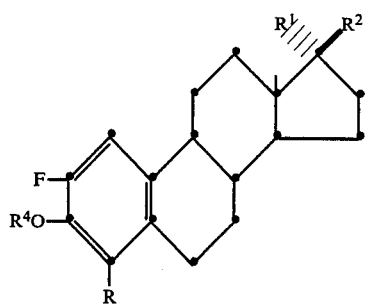

wherein R is H or F; $R^1$, when taken singly, is H or ethinyl; $R^2$, when taken singly is OH; $R^1$ and $R^2$, when taken together, are O= and $R^4$ is H or $CH_3$ but can be $CH_3$ only when $R^1$ is not H, sufficient to alleviate the symptoms of said estrogen-deficiency disease without increasing the risk in said human female of the development of cancer of estrogen-sensitive tissues, said dose not to exceed 2 mg./day.

5. A process according to claim 1 in which the fluoro estrogen administered is 2-fluoro-β-estradiol.

6. A process according to claim 2 in which the fluoro estrogen administered is 2-fluoro-β-estradiol.

7. A process according to claim 3 in which the fluoro estrogen administered is 2-fluoro-β-estradiol.

8. A process according to claim 4 in which the fluoro estrogen administered is 2-fluoro-β-estradiol.

9. A process according to claim 1 in which the fluoro estrogen administered is 2-fluoro-17α-ethinyl estradiol.

10. A process according to claim 2 in which the fluoro estrogen administered is 2-fluoro-17α-ethinyl estradiol.

11. A process according to claim 3 in which the fluoro estrogen administered is 2-fluoro-17α-ethinyl estradiol.

12. A process according to claim 4 in which the fluoro estrogen administered is 2-fluoro-17α-ethinyl estradiol.

* * * * *